United States Patent [19]
Fabry et al.

[11] Patent Number: 5,952,279
[45] Date of Patent: Sep. 14, 1999

[54] MILD DETERGENT MIXTURES

[75] Inventors: Bernd Fabry, Korschenbroich; Ansgar Behler, Bottrop, both of Germany

[73] Assignee: Henkel Kommanditgesellschaft auf Aktien, Duesseldorf, Germany

[21] Appl. No.: 08/793,960

[22] PCT Filed: Aug. 31, 1995

[86] PCT No.: PCT/EP95/03413

§ 371 Date: Mar. 7, 1997

§ 102(e) Date: Mar. 7, 1997

[87] PCT Pub. No.: WO96/07473

PCT Pub. Date: Mar. 14, 1996

[30]  Foreign Application Priority Data

Sep. 9, 1994 [DE] Germany ............... 44 32 130

[51] Int. Cl.⁶ ............... B01F 17/00; C11D 1/83
[52] U.S. Cl. ............ 510/276; 510/470; 510/446
[58] Field of Search .................. 510/126, 156, 510/159, 147, 123, 133, 152, 276, 446, 470

[56]  References Cited

U.S. PATENT DOCUMENTS

| | | | |
|---|---|---|---|
| 3,247,122 | 4/1966 | Schaafsma et al. | 252/135 |
| 3,247,123 | 4/1966 | Schrager et al. | 252/135 |
| 3,792,041 | 2/1974 | Yamagishi et al. | 260/234 |
| 4,207,198 | 6/1980 | Kenkare | 510/135 |
| 4,948,576 | 8/1990 | Verdicchio et al. | 424/59 |
| 5,312,932 | 5/1994 | Behler et al. | 554/90 |
| 5,322,957 | 6/1994 | Fabry et al. | 558/23 |
| 5,489,395 | 2/1996 | Behler et al. | 510/135 |
| 5,599,476 | 2/1997 | Behler et al. | 510/135 |
| 5,693,605 | 12/1997 | Isobe et al. | 510/499 |

FOREIGN PATENT DOCUMENTS

| | | |
|---|---|---|
| 0 117 135 | 8/1984 | European Pat. Off. . |
| 1 411 088 | 12/1965 | France . |
| 20 51 766 | of 0000 | Germany . |
| 14 67 564 | 10/1969 | Germany . |
| 42 29 442 | 3/1994 | Germany . |
| 43 00 325 | 7/1994 | Germany . |
| 824 654 | 12/1959 | United Kingdom . |
| 92/09569 | 6/1992 | WIPO . |
| 92/09570 | 6/1992 | WIPO . |
| 93/20171 | 10/1993 | WIPO . |
| 95/23582 | 9/1995 | WIPO . |

OTHER PUBLICATIONS

J. Am. Oil. Chem. Soc. 37, (1960) p. 171, month unavailable.
J. Oil Technol. Ass. Ind. (1972) p. 41, month unavailable.
Indian J. Pharm. Sci. 41, (1979) p. 181, month unavailable.
Tens. Surf. Det. 29, (1992) p. 342, month unavailable.
Parf. Kosm. 64, (1991) p. 463, month unavailable.
Surfactants in Consumer Products, J Falbe (ed.), Springer–Verlag, Berlin, 1987, pp. 101 to 103, month unavailable.
Tens. Surf. Det., 27, (1990) p. 350, month unavailable.
J. Am. Oil. Chem. Soc., 66 (1989) p. 1581, month unavailable.
Surfactants in Consumer Products, J Falbe (ed.), Springer–Verlag, Berlin, 1987, pp. 54 to 124, month unavailable.
Katalysatoren, Tenside und Mineralöladditive, Thieme Verlag, Stuttgart, 1978 pp. 123 to 217, month unavailable.
"Kosmetische Färbemittel" der Farbstoffkommission der Deutschen Forschungsgemeinschaft, published by Verlag Chemie, Weinheim, 1984, pp. 81 to 106, month unavailable.
Römpp Chemie Lexikon, Farbe & Regitz, pp. 3570 & 4217, date unavailable.

*Primary Examiner*—Jacqueline V. Howard
*Attorney, Agent, or Firm*—Ernest G. Szoke; Wayne C. Jaeschke; Real J. Granmaison

[57]  ABSTRACT

Surfactant mixtures providing improved dermal compatibility and foam stability contain
  (a) monoglyceride sulfates or monoglyceride ether sulfates, and
  (b) sugar surfactants selected from
    (b1) sucrose esters,
    (b2) sorbitan esters, and
    (b3) polysorbates, with the proviso that the ratio by weight of component (a) to component (b) is 75:25 to 50:50.

7 Claims, No Drawings

MILD DETERGENT MIXTURES

This application is a 371 of PCT/EP95/03413 Aug. 31, 1995.

BACKGROUND OF THE INVENTION

1. Field of the Invention

This invention relates to detergent mixtures with improved dermal compatibility containing monoglyceride (ether) sulfates and selected sugar surfactants, to surface-active formulations containing these mixtures and to the use of the mixtures for the production of surface-active formulations.

2. Discussion of Related Art

Formally, monoglyceride sulfates are products of the addition of sulfur trioxide to the primary hydroxyl group of a glycerol monofatty acid ester. Technically, however, they are complex anionic surfactant mixtures which are normally obtained by the simultaneous transesterification and sulfation of mixtures of triglycerides and glycerol and subsequent neutralization.

Monoglyceride sulfates are distinguished by satisfactory performance properties and good dermatological compatibility. Overviews on the production and properties of monoglyceride sulfates have been published, for example, by A. K. Biswas et al. in J. Am. Oil. Chem. Soc. 37, 171 (1960), R. Chamanial et al. in J. Oil Technol. Ass. Ind. 41 (1972) and J. K. Jain in Indian J. Pharm. Sci. 41, 181 (1979).

Unfortunately, the foaming behavior, especially in hard water, and dermal compatibility of monoglyceride sulfates and the corresponding ether sulfates are not entirely satisfactory for a number of applications.

Accordingly, the problem addressed by the present invention was to find a way of significantly improving the performance and dermal compatibility of monoglyceride (ether) sulfates.

DESCRIPTION OF THE INVENTION

The present invention relates to mild detergent mixtures containing (a) monoglyceride (ether) sulfates and (b) sugar surfactants selected from the group consisting of
   (b1) sucrose esters,
   (b2) sorbitan esters and/or
   (b3) polysorbates.

It has surprisingly been found that mixtures of monoglyceride sulfates or monoglyceride ether sulfates and the sugar surfactants mentioned lead to synergistically improved dermal compatibility and increased foaming power.

Monoglycerides and monoglyceride ether sulfates

Monoglyceride sulfates and monoglyceride ether sulfates are known anionic surfactants which may be obtained by the relevant methods of preparative organic chemistry. They are normally produced from triglycerides which are transesterified to the monoglycerides, optionally after ethoxylation, and subsequently sulfated and neutralized. The partial glycerides may also be reacted with suitable sulfating agents, preferably gaseous sulfur trioxide or chlorosulfonic acid [cf. WO 92/09569, WO 92/09570, Henkel KGaA]. If desired, the neutralized substances may be subjected to ultrafiltration to reduce the electrolyte content to the required level.

The monoglyceride (ether) sulfates to be used in accordance with the invention correspond to formula (I):

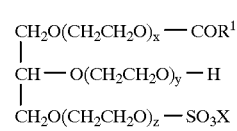

in which $R^1CO$ is a linear or branched acyl group containing 6 to 22 carbon atoms, x, y and z together are 0 or a number of 1 to 30 and X is an alkali metal or alkaline earth metal.

Typical examples of monoglyceride (ether) sulfates suitable for use in accordance with the invention are the reaction products of lauric acid monoglyceride, cocofatty acid monoglyceride, palmitic acid monoglyceride, stearic acid monoglyceride, oleic acid monoglyceride and tallow fatty acid monoglyceride and ethylene oxide adducts thereof with sulfur trioxide or chlorosulfonic acid in the form of the sodium salts. Monoglyceride sulfates corresponding to formula (I), in which $R^1CO$ is a linear acyl group containing 8 to 18 carbon atoms, are preferably used.

Sucrose esters

Sucrose esters, which are often also referred to as sugar esters, are well-known nonionic surfactants. These compounds are normally produced by transesterification of fatty acid methyl esters with sucrose in the presence of basic catalysts, for example pyridine or piperidine, in organic solvents [cf. DE-AS 2 051 766 (Day-Ichi; for solventless methods, cf. L. Guillardeau in Tens. Surf. Det. 29, 342 (1992))]. Mono-, di-, tri- and polyesters of the sucrose are formed according to the raw materials used and the reaction conditions selected, although in general it is only the monoesters and diesters which are of practical significance. An overview of this subject was published, for example, by N. Desai in Parf. Kosm. 64, 463 (1991). Information on the structure and properties of the substances can also be found in Surfactants in Consumer Products, J. Falbe (ed.), Springer-Verlag, Berlin, 1987, pages 101 to 103.

The sucrose esters correspond to formula (II):

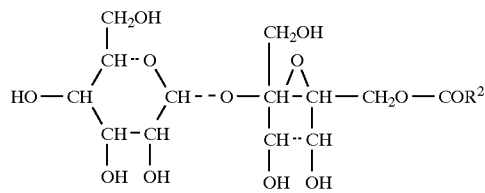

in which $R^2CO$ is an aliphatic acyl group containing 6 to 22 carbon atoms and 0 and/or 1, 2 or 3 double bonds. A monoester is represented by way of example in formula (II). It is obvious that the other hydroxyl groups, especially the primary hydroxyl groups, may also be esterified.

Typical examples of suitable sucrose esters, preferably sucrose monoesters and/or diesters, are transesterification products of sucrose with methyl esters of caproic acid, caprylic acid, 2-ethyl hexanoic acid, capric acid, lauric acid, isotridecanoic acid, myristic acid, palmitic acid, palmitoleic acid, stearic acid, isostearic acid, oleic acid, elaidic acid, petroselic acid, linoleic acid, linolenic acid, elaeostearic acid, arachic acid, gadoleic acid, behenic acid and erucic acid and the technical mixtures thereof obtained, for example, in the pressure hydrolysis of natural fats and oils, in the reduction of aldehydes from Roelen's oxosynthesis or in the dimerization of unsaturated fatty acids.

Technical sucrose monoesters and/or diesters of which the fatty acid component is derived from a technical $C_{12/18}$ or $C_{12/14}$ cocofatty acid cut are preferred.

Sorbitan esters

Sorbitan esters are products of the esterification or transesterification of sorbitol with fatty acids or fatty acid methyl esters at temperatures of 200 to 250° C. In a first step, sorbitol is dehydrated to form a mixture of 1,4- and 3,6-sorbitan [cf. S. Ropuszynski et al. in Tens. Surf. Det. 27, 350 (1990)], after which the sorbitan is converted into a mixture of mono-, di- and triesters in dependence upon the working conditions [cf. C. Akoh et al. in J. Am. Oil. Chem. Soc., 66, 1581 (1989) and Surfactants in Consumer products, J. Falbe (ed.), Springer-Verlag, Berlin, 1987, pages 101 to 103.

The sorbitan esters correspond to formula (III):

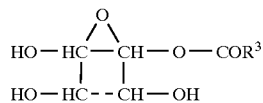
(III)

in which $R^3CO$ is an aliphatic acyl group containing 6 to 22 carbon atoms and 0 and/or 1, 2 or 3 double bonds. A monoester is represented by way of example in formula (III). It is obvious that the other hydroxyl groups may also be esterified.

Typical examples of suitable sorbitan esters, preferably sorbitan mono-, sesqui- and/or diesters, are formal esterification products of sorbitan with caproic acid, caprylic acid, 2-ethyl hexanoic acid, capric acid, lauric acid, isotridecanoic acid, myristic acid, palmitic acid, palmitoleic acid, stearic acid, isostearic acid, oleic acid, elaidic acid, petroselic acid, linoleic acid, linolenic acid, elaeostearic acid, arachic acid, gadoleic acid, behenic acid and erucic acid and the technical mixtures thereof obtained, for example, in the pressure hydrolysis of natural fats and oils, in the reduction of aldehydes from Roelen's oxosynthesis or in the dimerization of unsaturated fatty acids. Technical sorbitan mono-, sesqui- or diesters of which the fatty acid components are derived from a technical $C_{21/18}$ or $C_{12/14}$ cocofatty acid cut, lauric acid, palmitic acid, stearic acid or oleic acid are preferred.

Polysorbates

Polysorbates are ethoxylated sorbitan esters and are normally prepared by subsequent addition of ethylene oxide to the free hydroxyl groups of the sorbitan esters or by insertion into the carbonyl ester compounds. The substances correspond to formula (IV):

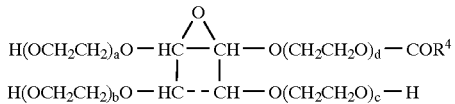
(IV)

in which $R^4CO$ is an aliphatic acyl group containing 6 to 22 carbon atoms and 0 and/or 1, 2 or 3 double bonds and the sum of (a+b+c+d) is a number of 1 to 50 and preferably 10 to 25. A monoester is again represented by way of example in formula (IV). It is obvious that the other hydroxyl groups may also be esterified.

Typical examples of suitable polysorbates, preferably ethoxylated sorbitan mono-, sesqui- and/or diesters, are products of the addition of on average 1 to 50 and preferably 1 to 15 moles of ethylene oxide to 1 mole of a formal esterification product of sorbitan with caproic acid, caprylic acid, 2-ethyl hexanoic acid, capric acid, lauric acid, isotridecanoic acid, myristic acid, palmitic acid, palmitoleic acid, stearic acid, isostearic acid, oleic acid, elaidic acid, petroselic acid, linoleic acid, linolenic acid, elaeostearic acid, arachic acid, gadoleic acid, behenic acid and erucic acid and the technical mixtures thereof obtained, for example, in the pressure hydrolysis of natural fats and oils, in the reduction of aldehydes from Roelen's oxosynthesis or in the dimerization of unsaturated fatty acids.

Technical ethoxylated sorbitan mono-, sesqui- or diesters of which the fatty acid component is derived from a technical $C_{12/18}$ or $C_{12/14}$ cocofatty acid cut, lauric acid, palmitic acid, stearic acid or oleic acid and which contain 10 to 25 moles of ethylene oxide per mole of ester are preferred.

The detergent mixtures according to the invention may contain the monoglyceride (ether) sulfates and the sugar surfactants selected in a ratio by weight of 99:1 to 1:99, preferably 75:25 to 25:75 and, more preferably, 50:50 to 80:20.

Surfactants

The detergent mixtures according to the invention may contain other anionic, nonionic, cationic and/or amphoteric surfactants.

Typical examples of anionic surfactants are alkyl benzene sulfonates, alkane sulfonates, olefin sulfonates, alkyl ether sulfonates, glycerol ether sulfonates, α-methyl ester sulfonates, sulfofatty acids, alkyl sulfates, fatty alcohol ether sulfates, glycerol ether sulfates, hydroxy mixed ether sulfates, fatty acid amide (ether) sulfates, mono- and dialkyl sulfosuccinates, mono- and dialkyl sulfosuccinamates, sulfotriglycerides, amide soaps, alkyl oligoglucoside sulfates and alkyl (ether) phosphates. If the anionic surfactants contain polyglycol ether chains, they may have a conventional homolog distribution although they preferably have a narrow homolog distribution.

Typical examples of nonionic surfactants are fatty alcohol polyglycol ethers, alkylphenol polyglycol ethers, fatty acid polyglycol esters, fatty acid amide polyglycol ethers, fatty amine polyglycol ethers, alkoxylated triglycerides, mixed ethers and mixed formals, alk(en)yl oligoglycosides, fatty acid N-alkyl glucamides and protein hydrolyzates (more particularly vegetable soyabased products). If the nonionic surfactants contain polyglycol ether chains, they may have a conventional homolog distribution although they preferably have a narrow homolog distribution.

Typical examples of cationic surfactants are quaternary ammonium compounds and esterquats, more particularly quaternized fatty acid trialkanolamine ester salts.

Typical examples of amphoteric or zwitterionic surfactants are alkyl betaines, alkyl amidobetaines, aminopropionates, aminoglycinates, imidazolinium betaines and sulfobetaines.

All the surfactants mentioned are known compounds. Information on their structure and production can be found in relevant synoptic works, cf. for example J. Falbe (ed.), (Surfactants in Consumer Products", Springer Verlag, Berlin, 1987, pages 54 to 124 or J. Falbe (ed.), "Katalysatoren, Tenside und Mineraloladditive", Thieme Verlag, Stuttgart, 1978, pages 123–217.

The detergent mixtures according to the invention may contain the additional surfactants mentioned above in quantities of 1 to 50% by weight and preferably in quantities of 5 to 25% by weight, based on the solids content of the mixtures.

Commercial Applications

The detergent mixtures according to the invention are distinguished by particularly advantageous foaming power and by synergistically improved dermal compatibility—properties which are important in the development of a number of surface-active formulations.

Accordingly, the present invention also relates to surface-active formulations containing these detergent mixtures which are defined in more detail in the following:

Powder-form heavy-duty detergents containing 10 to 30% by weight, based on the detergent, of the detergent mixtures according to the invention and typical auxiliaries and additives.

Liquid heavy-duty detergents containing 10 to 70% by weight, based on the detergent, of the detergent mixtures according to the invention and typical auxiliaries and additives.

Liquid light-duty detergents containing 10 to 50% by weight, based on the detergent, of the detergent mixtures according to the invention and typical auxiliaries and additives.

Fabric softeners containing 10 to 50% by weight, based on the softener, of the detergent mixtures according to the invention and typical auxiliaries and additives.

Manual dishwashing detergents containing 10 to 50% by weight, based on the detergent, of the detergent mixtures according to the invention and typical auxiliaries and additives.

Rinse aids containing 10 to 50% by weight, based on the rinse aid, of the detergent mixtures according to the invention and typical auxiliaries and additives.

Liquid cleaners and disinfectants containing 10 to 30% by weight, based on the cleaner/disinfectant, of the detergent mixtures according to the invention and typical auxiliaries and additives.

Bar soaps of the combination bar type containing 1 to 2% by weight, based on the bar soap, of the detergent mixtures according to the invention and typical auxiliaries and additives.

Syndet soaps containing 1 to 2% by weight, based on the syndet soap, of the detergent mixtures according to the invention and typical auxiliaries and additives.

Hair shampoos containing 10 to 30% by weight, based on the shampoo, of the detergent mixtures according to the invention and typical auxiliaries and additives.

Hair rinses containing 10 to 30% by weight, based on the hair rinse, of the detergent mixtures according to the invention and typical auxiliaries and additives.

Hair colorants containing 10 to 30% by weight, based on the colorant, of the detergent mixtures according to the invention and typical auxiliaries and additives.

Hair wave sets containing 10 to 30% by weight, based on the wave set, of the detergent mixtures according to the invention and typical auxiliaries and additives.

Foam baths containing 10 to 30% by weight, based on the foam bath, of the detergent mixtures according to the invention and typical auxiliaries and additives.

Textile and fiber auxiliaries containing 1 to 30% by weight, based on the auxiliary, of the detergent mixtures according to the invention and typical auxiliaries and additives.

Leather oiling formulations containing 1 to 30% by weight, based on the oiling formulation, of the detergent mixtures according to the invention and typical auxiliaries and additives.

Flotation aids containing 1 to 30% by weight, based on the flotation aid, of the detergent mixtures according to the invention and typical auxiliaries and additives.

Auxiliaries for the dewatering of solids containing 1 to 30% by weight, based on the auxiliary, of the detergent mixtures according to the invention and typical auxiliaries and additives.

Auxiliaries and additives

Laundry detergents, dishwashing detergents, cleaners and fabric softeners based on the detergent mixtures according to the invention may contain, for example, builders, salts, bleaching agents, bleach activators, optical brighteners, redeposition inhibitors, solubilizers and enzymes as further auxiliaries and additives in addition to the surfactants already mentioned.

Typical builders are sodium aluminium silicates (zeolites), phosphates, phosphonates, ethylenediamine tetraacetic acid, nitrilotriacetate, citric acid and/or polycarboxylates.

Suitable salts and extenders are, for example, sodium sulfate, sodium carbonate or sodium silicate (waterglass). Typical individual examples of other additives are sodium borate, starch, sucrose, polydextrose, TAED, stilbene compounds, methyl cellulose, toluene sulfonate, cumene sulfonate, long-chain soaps, silicones, mixed ethers, lipases and proteases.

Hair shampoos, hair lotions or foam baths may contain emulsifiers, such as alkoxylated fatty alcohols or sorbitan esters for example, as further auxiliaries and additives in addition to the surfactants already mentioned.

Suitable superfatting agents are such substances as, for example, polyethoxylated lanolin derivatives, lecithin derivatives and fatty acid alkanolamides, the fatty acid alkanolamides also serving as foam stabilizers.

Suitable thickeners are, for example, polysaccharides, more particularly xanthan gum, guar guar, agar agar, alginates and tyloses, carboxymethyl cellulose and hydroxyethyl cellulose, also relatively high molecular weight polyethylene glycol monoesters and diesters of fatty acids, polyacrylates, polyvinyl alcohol and polyvinyl pyrrolidone and electrolytes, such as sodium chloride and ammonium chloride.

Suitable biogenic agents are, for example, plant extracts and vitamin complexes.

Typical film formers are, for example, chitosan, microcrystalline chitosan, quaternized chitosan, polyvinyl pyrrolidone, vinyl pyrrolidone/vinyl acetate copolymers, polymers of the acrylic acid series, quaternary cellulose derivatives and similar compounds.

Suitable preservatives are, for example, phenoxyethanol, formaldehyde solution, parabens, pentanediol or sorbic acid.

Suitable pearlescers are, for example, glycol distearic acid esters, such as ethylene glycol distearate, and fatty acid monoglycol esters.

The dyes used may be any of the substances suitable and licensed for cosmetic purposes, as listed for example in the publication entitled "Kosmetische Facrbemittel" der Farbstoffkommission der Deutschen Forschungsgemeinschaft, published by Verlag Chemie, Weinheim, 1984, pages 81–106. These dyes are normally used in concentrations of 0.001 to 0.1% by weight, based on the mixture as a whole.

The total content of auxiliaries and additives may be 1 to 50% by weight and is preferably 5 to 40% by weight, based on the particular formulation.

Finally, the present invention relates to the use of the detergent mixtures according to the invention for the production of liquid or solid surface-active formulations in which they may be present in quantities of 1 to 99% by weight and preferably 10 to 90% by weight, based on the solids content of the formulation.

EXAMPLES

I. Surfactants used

A1) $C_{12/18}$ coconut monoglyceride sulfate sodium salt

B1) Sucrose mono-/dilaurate
B2) Sorbitan monolaurate DEHYMULS® SML, Henkel KGaA, Düsseldorf, FRG
B3) Polysorbate (sorbitan monolaurate 20 EO) EUMULGINO® SML-20, Henkel KGaA, Däusseldorf, FRG II. Results of performance tests Foaming power was determined in accordance with DIN 53 902, Part 2 (Ross Miles Test) using 1% by weight surfactant solutions in water with a hardness of 16° d. The temperature was 20° C. The basic foam and foam volume after 5 minutes were determined.

The irritation potential was determined by OECD Method No. 404 and in accordance with EEC Directive 84/449 EEC, Pt.B.4. The total irritation scores shown were formed from the irritation scores obtained after 24, 48 and 72 hours. The total irritation score for a 100% $C_{12/18}$ coconut fatty acid monoglyceride sulfate sodium salt determined in comparison test C1 was put at 100% and the total irritation scores obtained in the other tests were related to that score.

The results are set out in Table 1 (percentages as % by weight).

TABLE 1

Foaming Power and Irritation Potential

| Ex. | [A1] | B | [B] | Foam Height [ml] Immediately | After 5 mins. | Total Irritation Score %-Rel |
|---|---|---|---|---|---|---|
| 1 | 50 | B1 | 50 | 510 | 390 | 60 |
| 2 | 70 | B1 | 30 | 540 | 400 | 55 |
| 3 | 70 | B2 | 30 | 530 | 390 | 55 |
| 4 | 70 | B3 | 30 | 550 | 410 | 55 |
| C1 | 100 | — | — | 500 | 300 | 100 |
| C2 | 0 | B1 | 100 | 200 | 100 | 45 |
| C3 | 0 | B2 | 100 | 200 | 100 | 48 |
| C4 | 0 | B3 | 100 | 250 | 110 | 43 |

What is claimed is:

1. Surfactant mixtures providing improved dermal compatibility and foam stability, said surfactant mixtures comprising
   (a) monoglyceride sulfates or monoglyceride ether sulfates, and
   (b) sugar swrfactants selected from the group consisting of
      (b1) sucrose esters,
      (b2) sorbitan esters, and
      (b3) polysorbates,
with the proviso that the ratio by weight of component (a) to component (b) is 75:25 to 50:50: wherein said monoglyceride sulfates or monoglycecride ether sulfates correspond to formula (I):

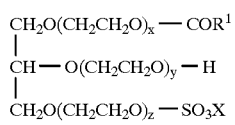

in which $R^1CO$ is a linear branched acyl group containing 6 to 22 carbon atoms, x, y and z together are 0 or a number of 1 to 30, and X is an alkali metal, or alkaline earth metal, and said sucrose esters correspond to formula (II):

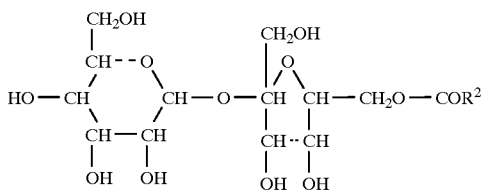

in which $R^2CO$ is an aliphatic acyl group containing 6 to 22 carbon atoms and 0, or 1, 2 or 3 double bonds.

2. Surfactant mixtures according to claim 1 wherein said monoglyceride sulfates or monoglyceride ether sulfates correspond to formula (I):

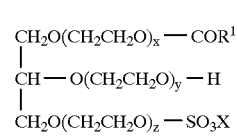

which $R^1CO$ is a linear or branched acyl group containing 6 to 22 carbon atoms, x, y and z together are 0 or a number of 1 to 30, and X is an alkali metal or alkaline earth metal.

3. Surfactant mixtures according to claim 1 wherein said sucrose esters correspond to formula (II):

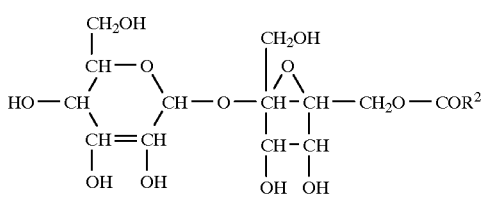

in which $R^2CO$ is an aliphatic acyl group containing 6 to 22 carbon atoms and 0, or 1, 2 or 3 double bonds.

4. Surfactant mixtures according to claim 1 wherein said sorbitan esters correspond to formula (III):

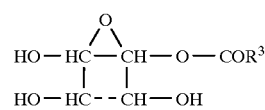

in which $R^3CO$ is an aliphatic acyl group containing 6 to 22 carbon atoms and 0 or 1, 2 or 3 double bonds.

5. Surfactant mixtures providing improved dermal compatibility and foam stability, said surfactant mixtures comprising
   (a) monoglyceride sulfates or monoglyceride ether sulfates, and
   (b) sugar surfactants selected from the group consisting of
      (b1) sucrose esters,
      (b2)sorbitan esters, and
      (b3)polysorbates,
with the proviso that the ratio by weight of component (a) to component (t) is 75:25 to 50:50; wherein said monoglyceride sulfates or monoglyceride ether sulfate correspond to a formula (I):

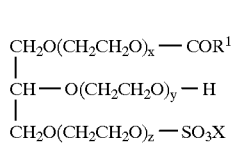
(I)

in which $R^1CO$ is a linear or branched acyl group containing 6 o 22 carbon atoms, x, y and z together are 0 or a number of 1 to 30, and X is an alkali metal or alkaline earth metal, said sucrose esters correspond to formula (II):

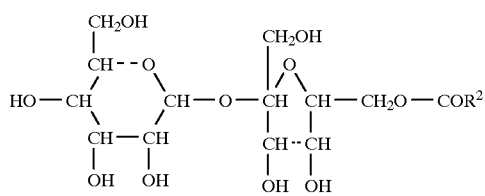
(II)

in which $R^1CO$ is an aliphatic acyl group containing 6 to a carbon atoms and 0, or 1, 2 or 3 double bonds, said sorbitan esters correspond to formula (III):

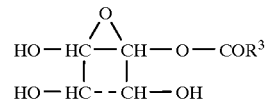
(III)

in which $R^3CO$ is aliphatic acyl group containing 6 to 22 carbon atoms and 0, or 1, 2 or 3 double bonds, and wherein said polysorbates correspond to formula (IV).

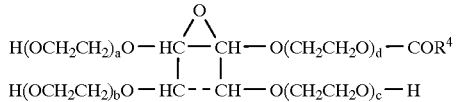
(IV)

in which $R^4 CO$ is an aliphatic acyl group containing 6 to 22 carbon atoms and 0 or 1, 2 or 3 double bonds and the sum of (a+b+c+d) is a number of 1 to 50.

6. Surfactant mixtures according to claim 1 present in a detergent composition.

7. Surfactant mixtures according to claim 6 wherein said detergent composition is a granular heavy-duty composition and said surfactant mixtures are present therein in an amount 10% to 30% by weight, based on the weight of said detergent composition.

* * * * *